United States Patent [19]

Bruening et al.

[11] 4,193,963

[45] Mar. 18, 1980

[54] APPARATUS FOR THE DETERMINATION OF CHEMICAL COMPOUNDS BY CHEMILUMINESCENCE WITH OZONE

[75] Inventors: Wilhelm Bruening; Ináí M. R. de Andrade Bruening; Francisco J. Martinez Concha, all of Rio de Janeiro, Brazil

[73] Assignee: Petroleo Brasileiro S.A.-Petrobras, Rio de Janeiro, Brazil

[21] Appl. No.: 803,916

[22] Filed: Jun. 6, 1977

Related U.S. Application Data

[63] Continuation-in-part of Ser. No. 614,981, Sep. 19, 1975, abandoned.

[30] Foreign Application Priority Data

Sep. 20, 1974 [BR] Brazil ................................ 007833

[51] Int. Cl.² .................. G01N 21/24; G01N 33/00
[52] U.S. Cl. ............................ 422/52; 23/230 M; 422/70; 422/89
[58] Field of Search ......... 23/230 R, 230 HC, 230 M, 23/232 R, 232 E, 253 R, 254 R, 254 E; 422/52, 98

[56] References Cited

U.S. PATENT DOCUMENTS

| | | | |
|---|---|---|---|
| 3,520,660 | 7/1970 | Webb | 23/253 R |
| 3,659,100 | 4/1972 | Anderson et al. | 23/230 R |
| 3,710,107 | 1/1973 | Warren et al. | 23/230 R |
| 3,713,773 | 1/1973 | Fontijn et al. | 23/232 E |
| 3,730,686 | 1/1973 | Breitenbach et al. | 23/232 E |
| 3,746,514 | 7/1973 | Colvin et al. | 23/232 E |

OTHER PUBLICATIONS

Fontijn et al., Eviron. Sci. & Tech., pp. 1157–1163, vol. 9., No. 13, Dec. 1975 Homo. Gas Phase Chemiluminescence Meas. of Reactive Hydrocarbons Air Pollutants by Reaction with Oxygen Atoms.
Kummer et al., Chemiluminescent Reactions of Ozone With Olefins & Sulfides., Envir. Science & Tech., vol. 15, No. 10, 10/71. Pitts; Chem. Reactions of Ozone with Olefins & Organic Sulfides, Advances in Chem. Series 113, ACS., pp. 246–254 (1972).
Ozone Induced Chem. of Organic Compounds Science, vol. 154, (1966).
Kinetics of the Fast Gas Phase Reaction between Ozones Nitric Oxide, Johnston et al.; J of Chem. Physics, Vol. 22, No. 4, 4/1954.

*Primary Examiner*—Michael S. Marcus
*Attorney, Agent, or Firm*—Sughrue, Rothwell, Mion, Zinn and Macpeak

[57] ABSTRACT

The invention relates to a process and detector for determining organic and inorganic chemical substances by chemiluminescence with ozone, the selectivity and specificness of the detector being a function of the degree of reactivity of the chemical substances with ozone in distinct temperature ranges. The chemiluminescence reaction takes place in the reaction chamber of the detector, in the absence of oxygen, and with thermal control. The detector comprises the following units: ozone generator, reaction chamber, discharge means for gases issuing from the reaction chamber, an optical system, a photomultiplier, amplifier data transformer and recorder.

4 Claims, 7 Drawing Figures

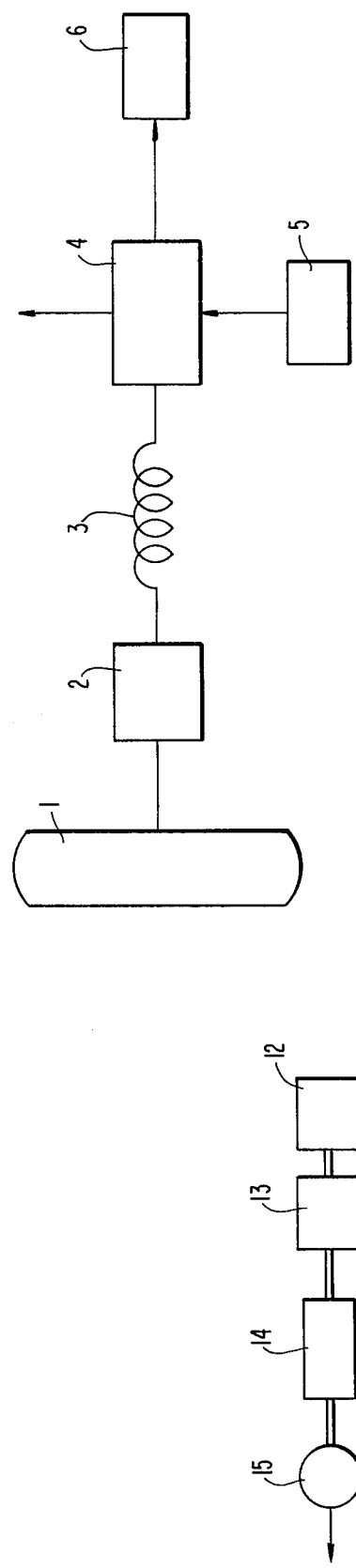
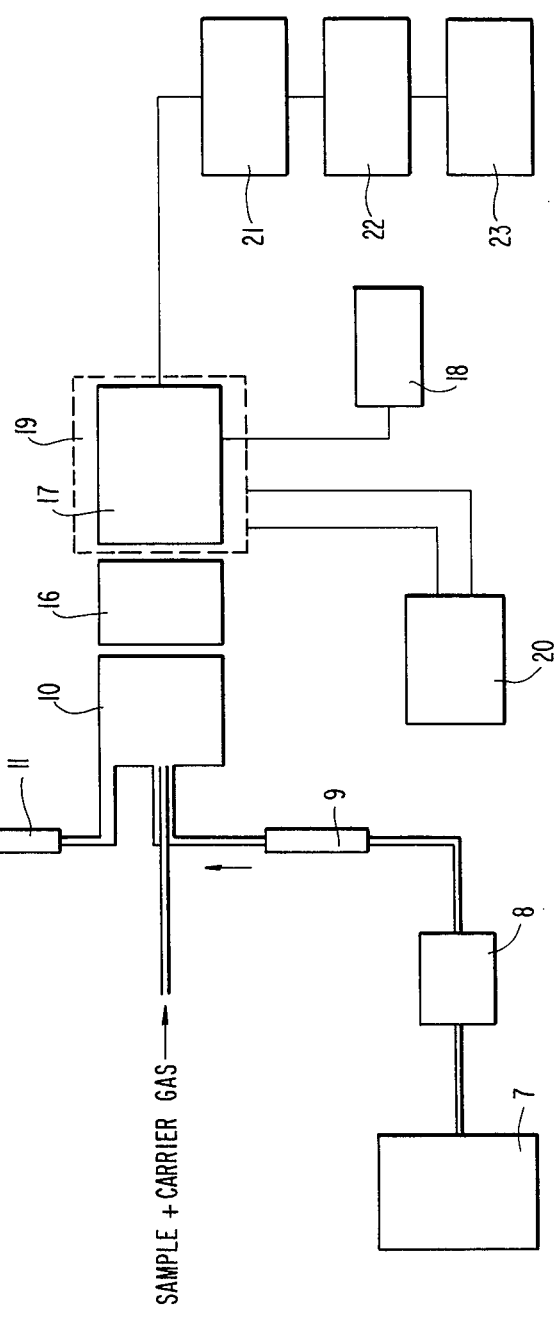

APPARATUS FOR THE DETERMINATION OF CHEMICAL COMPOUNDS BY CHEMILUMINESCENCE WITH OZONE

CROSS-REFERENCE TO RELATED APPLICATIONS

The present application is a continuation-in-part application of Ser. No. 614,981, filed Sept. 19, 1975, now abandoned.

BACKGROUND OF THE INVENTION

1. Field of the Invention

The present invention relates to a process and detector for the determination of chemical compounds by chemiluminesence with ozone.

Essentially the process of the present invention consists in mixing vapors of chemical substances with a flow of ozone in a special reaction chamber or, more specifically, in a detector in which these substances are subjected to the ozone attack. From this reaction results the emission of luminous radiation, called chemiluminescene, which may or may not be transmitted through an optical system and is directed to a photomultiplier tube. The current generated in the photomultiplier tube is amplified in an amplifier and recorded in any convenient graphic system. In this way qualitative and quantitative determinations can be made of organic and inorganic substances capable of emitting chemiluminescence upon reacting with ozone.

When a gaseous mixture is passed through a chromatographic column, and the components thus separated are introduced into the reaction chamber, according to the present invention, and mixed with ozone so that a reaction and emission of luminous radiation will take place, the reaction chamber is embodied by a detector for gas chromotography determinations.

2. Description of the Prior Art

Numerous detectors of chemical substances are already being used in gas chromatography. The most well-known are the following:

I—Thermal detectors: detector of thermal conductivity; thermal absorption detector; flame detectors, such as hydrogen flame temperature detectors, of flame emmissivity detectors, or hydrogen flame ionization detectors, of flame photometric detectors, of alkaline flame ionization detectors.

II—Detectors of non-radioactive ionization: thermoionic detector, photoionization detector, gas discharge detectors.

III—Detectors of radioactive ionization sources: detector of square section, argon detector, detector of electronic mobility, detector of electronic capture.

IV—Titrimetric or coulometric detectors.

V—Various detectors, results of corresponding adaptations of radiation counters, gravimetric, potentiometric and voltametric devices, analytical instruments, such as mass spectrometers, infrared or ultraviolet spectrophotometers, atomic absorption spectrometers, and the like.

Among the detectors used in gas chromatography the most common ones are those of thermal conductivity, of hydrogen flame ionization, electronic capture, alkaline flame ionization, and flame photometry.

The detector of thermal conductivity using thermistors or a heated filament and also called katharometer is one of the oldest and still the most widely used. With this detector the thermal conductivity of the gaseous mixture entering a sensitive cell is compared with the thermal conductivity of the pure carrier gas which flows constantly through the reference cell. It is a differential detector sensing the concentration of the substances present in the carrier gas, and a universal detector capable of responding to any vaporizable substance other than that used as the carrier gas.

In the hydrogen flame ionization detector the substances issuing from the chromatographic column are mixed with a hydrogen stream and burnt in a small burner, in the presence of air, producing a flame which is invisible to the naked eye. The temperature of the hydrogen flame is sufficient to ionize an organic substance, the ions of which when collected on electrodes, generate an electric current which is then amplified and transmitted to the graphic recorder. This is a specific detector for organic substances, insensitive to inorganic substances, such as fixed gases and water. The detector responds to the total mass of the burnt substance per time unit.

The detector of electronic capture employs a radioactive source to generate the ions to be measured by the detector. The radioactive source produces free electrons of great velocity which are captured by the molecules of the carrier gas used, forming negative stable ions or charged atoms, and thus generating a current. The capability of capturing free electrons is dependent on the electronic affinity of each molecule. If an organic substance separated in a chromatographic column enters the chamber of the detector and if this substance has greater electronic affinity than that of the carrier gas, some of the electrons will be captured and the initial current reduced in dependence on the quantity of the substance present and on its electron affinity, generating a signal which is recorded. This is an extremely sensitive detector. However, only substances having this property of electron capture can be detected, such as halogen containing compounds, nitrates, conjugated carbonyls and some organometallic compounds.

The alkaline flame detector is similar in operation and structure to the hydrogen flame ionization detector, the difference residing in the fact that a small quantity of an alkali salt, normally cesium bromide or rubidium sulphate, is placed close to the flame. The salt may be in the form of a tablet or it may cover a fabric or threads of various geometric configurations. When the hydrogen flame of the substance to be analysed burns in the presence of a weak current of air near an alkali salt, a current is generated which is about 100 times greater than that of the common hydrogen flame. This current increases considerably when the substance to be burnt contains phosphorus or halogen. Although the theoretic basis of the functioning of such a detector is still unknown, this is a device widely used in the determination of organophosphorus compounds in pesticides and polluents. It is a detector of great specific sensitivity for compounds containing phosphorus and for some compounds containing halogen.

The flame photometry detector is based on the fact that a hydrogen flame emits light in the presence of air. The carrier gas transporting a substance separated in the chromatographic column is mixed with an oxygen enriched air stream, passed on to a burner, and at the exit thereof hydrogen is added. The resulting gas mixture contains hydrogen in excess for complete combustion with the oxygen present. The luminous radiation caused by this combustion impinges upon a mirror and is reflected on to an optical filter which selects the desired wavelength (526 millimicrons for phosphorus-containing substances and 394 millimicrons for sulphur-containing substances). Subsequently it passes to a photomultiplier tube, the current of which is amplified and recorded. This is a specific selective detector for sulphur-and/or phosphorus containing substances, since the observed emittance results from the formation of molecular specimens of $S_2$ and HPO during the burning in the hydrogen flame. It is a highly sensitive detector capable of detecting nanograms and is much used in pollution control and determination. It may be constructed as a channel so that only one type of substance is determined, according to the filter chosen. It may also comprise two channels, each furnished with an appropriate filter so as to detect sulphur- and phosphorus-containing compounds at the same time.

The functioning principle of the detector according to the invention is entirely different from that of the detectors described above, especially from that of the flame photometry detector because, although luminous emission does occur, there is no combustion, a fact requiring peculiar characteristics of the reaction chamber, as will become apparent from the specification below.

Chemiluminescence was already made use of in pollution control to determine ozone in the atmosphere. In this case the stream containing ozone is mixed with an ethene flow to provoke a reaction and consequently the generation of chemiluminesence, for instance as described by W. A. Kummer, J. N. Pitts, Jr. and R. P. Steer in the article "Chemiluminescent Reactions of Ozone with Olefins and Sulfides" in Environmental Science & Technology, 5 (1): 1045-1047, (1971). Also, the ozone may be applied to act on a coloring substance, for instance Rodamine B as cited by W. R. Seitz and M. P. Neary in an article entitled "Chemiluminescence and Bioluminescence in Chemical Analysis" published in Analytical Chemistry, 46/2/188A-202A, (1974).

Also chemiluminescence by reaction with ozone was already used in the determination of nitrogen oxides, NO and $NO_2$, for control of atmospheric pollution. In this case an atmosphere sample is caused to react with ozone in a chamber equipped with a photometric detector. Chemiluminescence results from the reaction of the ozone with NO in the wavelength range of 0.6 to 3.0 microns. Normally the devices used comprise a reduction zone containing activated carbon so as to convert $NO_2$ into NO. They determine the total of nitrogen oxides. The $NO_2$ concentration then is the difference between the oxide total and the NO concentration.

In the above cases the chemiluminescence produced by the reaction of ozone was used only in very specific instances in which the substance to be determined was the ozone proper or an inorganic gas such as NO.

SUMMARY OF THE INVENTION

The object of the present invention, to be shown afterwards, is to determine quantitatively and qualitatively organic and inorganic compounds present in a gaseous mixture using the chemiluminescence produced in the reaction of such compounds with ozone.

Up to now only one kind of substance, for instance ethylene, has been used to detect a low quantity of ozone as atmospheric pollutant.

In the present invention, on the contrary, there is a mixture of substances from different classes which react with ozone and which can be detected.

None of the known devices making use of chemiluminescence are suitable or adaptable for use in analysing of effluents from chromatographic columns.

The present invention provides a detector permitting the determination of organic and inorganic substances which, when brought into contact with ozone under certain conditions, emit luminescence, called chemiluminescence. The direct or indirect measuring of the luminescence is the parameter which indicates the presence or the quantitative content of the substances.

This determination is of great advantage in that it can be systematic, precise and continuous.

It is the object of the present invention to provide an apparatus capable of detecting any organic or inorganic chemical substance provided it emits chemiluminescence when reacting with ozone.

Another object of the invention is to provide an apparatus with a reaction chamber equipped with means to permit alterations in the operating conditions of the reaction chamber so as to cause the ozone to react with the different types of organic and inorganic chemical substances.

It is also an object of the present invention to enable the determination of substances having different chemical structures and molecular weights by measuring the intensity of the luminescence emitted by successively selecting the wavelength ranges of the luminescent radiation. This selectivity is possible since the apparatus is provided with optical and electronic systems permitting not only radiation selection but also amplification and recording of the signals generated.

It is yet another object of the invention to make use of the selectivity of the emission of luminescence of different types of chemical substances in the presence of ozone when specific temperature conditions prevail. In accordance with this object it is possible, once the temperature range is chosen within which a certain type of substance emits luminescence in the presence of ozone, to carry out a specific and selective determination of different substances of the same kind which differ in molecular weight or characteristics of structural configuration.

Another object of the invention is to allow chemical substances effluents from a chromatographic column to be detected when introduced in the reaction chamber.

Finally, it is an object of the invention to enable the detection of chemical substances taken directly from various sampling points along a production line or from storage facilities.

BRIEF DESCRIPTION OF THE DRAWINGS

These and other advantages and characteristics of the process and apparatus according to the invention will be better understood with the aid of the following description and the accompanying drawings, in which:

FIG. 1 is a diagrammatic representation of a gaseous phase chromatographic analysis system for fluid chemical mixtures, using an ozone detector according to the invention, FIG. 2 is a detailed diagrammatic representation of the component parts of the entire detecting system, i.e., of the reaction chamber unit and of the optical and recording system forming the detector proper according to the invention.

Figure 3:
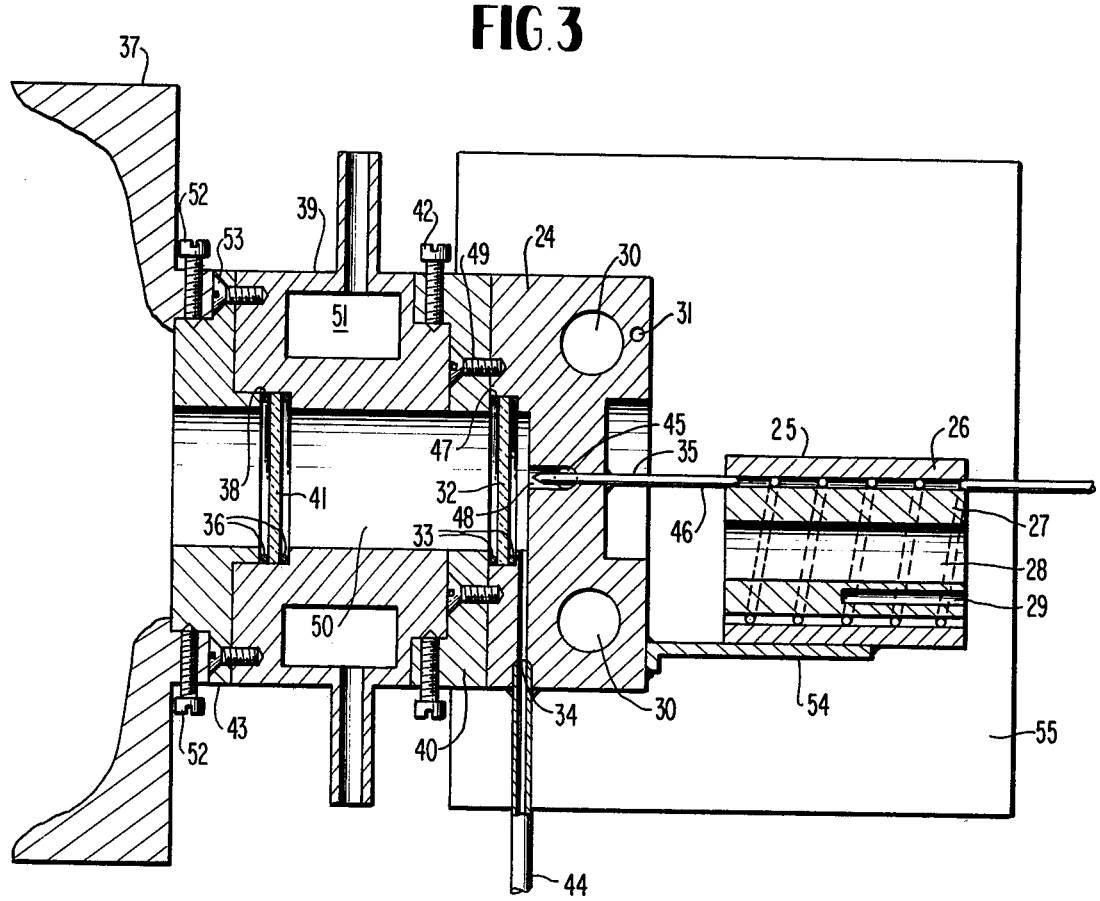
FIG. 3 is a detailed sectional side elevational view of the reaction chamber of the detector according to the invention.

The present invention provides a process for the qualitative and/or quantitative measurement of one or more specific chemical compounds or one or more classes of chemical compounds, capable of reacting with ozone to emit luminescence, contained in a gaseous mixture, comprising contacting said one or more chemical compounds or classes of chemical compounds with ozone in a reaction zone maintained at a predetermined temperature and under a super-atmospheric pressure to produce chemiluminescence and optically detecting the produced chemiluminescence to provide an electrical signal representative thereof. The present invention also provides an apparatus for the qualitative and/or quantitative measurement of one or more specific chemical compounds or one or more classes of chemical compounds, capable of reacting with ozone to emit luminescence, contained in a gaseous mixture.

DETAILED DESCRIPTION OF THE INVENTION

FIG. 1 shows a diagram of a gaseous chromatography system using the ozone detector according to the present invention. A carrier gas (helium, nitrogen, argon, or any other inert gas) supplied by a gas reservoir 1 is passed through liquid or gaseous sampling devices 2, and subsequently through the chromatographic column 3. At a certain point in time a liquid or gaseous sample is injected into the sampling device and passed on to the column in which its components are separated as they travel through the column. Together with the carrier gas (helium, nitrogen, argon, or any other inert gas) these components emerge from the column and are introduced into the detector 4 where they react with ozone supplied by a generator 5 so as to produce chemiluminescent radiation which will emit an electrical signal to be recorded in recorder 6.

FIG. 2 shows the component parts of the detector according to the invention in greater detail. As will be seen, the detector comprises an ozone generator 7 with flow regulator 8 and rotameter 9 to control the gas production, an exhaust gas system for the gases issuing from the reaction chamber 10. These gases comprise the ozone-sample reaction gas, the carrier gas introduced together with the sample, and any excess of ozone. The exhaust system proper comprises a rotameter 11, a trap 12 to eliminate the excess ozone, a discharge regulator 13, a vacuum regulator 14, and finally a vacuum source 15. The provision of the exhaust gas trap is necessary because of the fact that, ozone being a toxic and explosive gas, any excess thereof not consumed in the detector must be eliminated, this being achieved by passing it through the trap which contains a substance to eliminate it chemically, such as sodium thiosulphate or potassium iodide.

The discharge regulator 13 and the vacuum regulator 14 are needed to control the flow of exhaust products accurately from the reaction chamber 10. The vacuum source 15, by means of said discharge regulator 13 and vacuum regulator 14, evacuates only the trap, without making a vacuum in the reaction chamber 10, the pressure of which remains superatmospheric at all times.

The gases enter the reaction chamber 10 at a superatmospheric pressure, whether they come from a chromatographic column or from a production line. This occurs because the gaseous effluent from a chromatographic column is driven by carrier gas flow which, of course, is provided with a positive pressure, necessary to overcome the resistances inside the column. So, the exhaust gases from said column are expelled at a positive pressure. In the case of gases from a production line, they are provided with positive pressure as a necessary condition for sampling the said gases. In the same way, ozone must be injected into the reaction chamber also at a superatmospheric pressure. Thus, the pressure inside the reaction chamber 10 is maintained at a superatmospheric value, which may be in a range between 0.01 to 2.0 atm gage pressure or 1.01 to 3.0 atm absolute pressure.

When the reaction is completed the exhaust gases are driven out from the reaction chamber 10 by their own pressure to the liquid trap 12. However, if the flow of gases is not controlled by means of an exhaust gas system as described above, said flow will be intermittent because the gases have to pass through the liquid column in the trap 12 and this passing through will cause pulsation in the pressure. Such pulsation will interfere with the pressure in the reaction chamber 10, thus rendering it impossible to keep the conditions inside the reaction chamber constant.

To eliminate harmful effects of the pulsation, a gentle suction is applied to the system. By using a vacuum pump equipped with a vacuum regulator 14, a discharge regulator 13 and a rotameter 11, it is possible to obtain a very low and rigidly controlled suction, which is enough to assure an even flow of the exhaust gases from the reaction chamber but not enough to lower the reaction chamber pressure. The reaction chamber 10 will be described in more detail in connection with FIG. 3.

The optical system 16 consists of a filter or filter assembly or of a monochromator, depending on the determination to be made. A photomultiplier tube 17 is fed from a high voltage source 18 and provided with a jacket 19 for circulation of a cooling medium supplied by a thermostatic circulator 20.

An amplifier-discriminator 21 serves to amplify the signal received from the photomultiplier 17, eliminating electric noise and standardizing the pulses received.

A data converter 22 is used to transform the amplifier signal so that it can be recorded.

The recorder 23 which may be a potentiometer of magnetic type, may be connected in series or parallel with an integrator or computer. Thus, it is possible to have a recording and/or control and handling means for the data obtained.

FIG. 3 is a sectional elevation of the detector, i.e. of the reaction chamber and its various component parts.

The reaction chamber comprises a metal chamber 24 which must be made of corrosion-resistant material which will resist corrosion by the products used in the process. By way of example, the recommended materials are aluminum and stainless steel. Furthermore, the material must be chemically inert to ozone.

Figure 4:
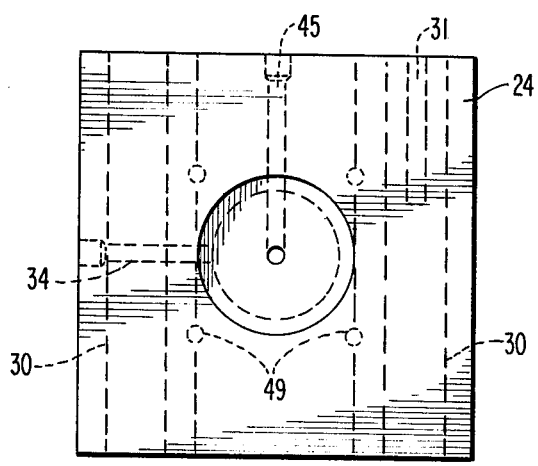
FIG. 4 is a cross sectional view of the reaction chamber.

Chamber 24 comprises:

(a) two openings 30 for insertion of heating cartridges;
(b) one opening 31 for insertion of a thermocouple, the electrical connections of the heating cartridges and thermocouple, which are not shown in FIG. 3, leading to a temperature control device responsible for the heating and temperature control of the chamber 24;

(c) a bore 34 to which a reaction gas exhaust tube 44 is connected;

(d) a bore 45, shown in sectional elevation in FIG. 4, for admission of ozone into the chamber 24;

(e) a bore 35 into which is inserted a tube 46 through which the sample and the carrier gas issuing from the chromatographic column are admitted into the chamber;

(f) a recess 47 into which a quartz window 32 is inserted, perfect sealing between the quartz window 32 and the surface of the recess 47 as well as with an adapter 40 being established by sealing rings 33; and (g) internally threaded bores in which the adapter 40 is fastened by screws 49.

Bore 35 located on the central axis of chamber 24 extends at right angles with respect to bore 45, and the apex of the angle thus formed lies in a recess 48 of chamber 24. Bore 34 which serves to exhaust the reaction gases, extends perpendicularly with respect to the plane formed by bores 35 and 45.

The sealing rings 33 for the quartz windows 32 are made from a material resisting the operating conditions of the metal chamber 24.

Tube 46 through which the gases issuing from the chromatographic column flow into the chamber, is inserted in such way into the bore 35 that the free end of tube 46 is located in an appropriate region of the recess 48 sufficiently close to bore 45 through which the ozone is admitted to facilitate the reaction with ozone.

Between chamber 24 and photomultiplier 37 there are disposed the adapter 40, a cooler 39, and an adapter 43. Adapter 40 is secured to the chamber 24 by a sufficient number of screws 49 to provide the necessary fixation.

Cooler 39 consists of a metal body with hollow interior 50 extending along the whole length of the central axis and having an inner diameter which corresponds to that of the interior of chamber 24 where the reaction with ozone takes place. The metal body of the cooler is provided with an internal channel 51 for circulation of the cooling liquid. Another recess 38 is formed in the cavity 50, into which a quartz window 41 is inserted.

Sealing between the quartz window 41 and the walls of the recess 38 and of the adaptor 43 is established by seals 36 which must be made from a material resisting the temperature conditions of the cooler 39.

Cooler 39 is likewise provided with means for fixing the adapters 40 and 43, in the present example embodied by internally threaded bores, receiving screws 42 and 53, respectively, and also with means for fixing the photomultiplier tube 37, in the present example made up by internally threaded bores receiving screws 52.

Part of the gas admission tube 46 through which the gases from the chromatographic column flow is formed helically so as to permit heating of the gases in order to avoid condensation and allow them to enter the reaction chamber 24 at a suitable temperature for the chemiluminescent reaction. This particular helical part is to provide good conditions for adequate heating. The radius of curvature of the helix is so selected that the tube may be received in the hollow heating space provided in a heater 25.

Figure 5:
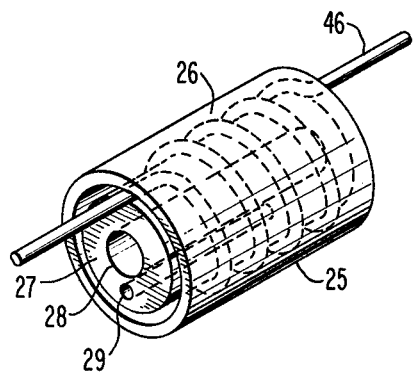
FIG. 5 is a perspective view of a heater used in the reaction chamber.

For proper functioning, the heater 25 is formed from a hollow cylinder 26 into which another hollow cylinder 27 is fitted. The inner diameter of hollow cylinder 26 is greater than the outer diameter of hollow cylinder 27 to such an extent that when cylinder 27 is received in cylinder 26, the helically coiled part of tube 46 can be placed in the annular space thus formed. It will be obvious to those skilled in the art that the annular space between the two cylinders 26 and 27 must be slightly larger than the outer diameter of the gas admission tube 46. These details are shown in FIG. 5.

Hollow cylinder 27 comprises a cylindrical cavity 28, the diameter of which is so selected that the cylindrical heating cartridge fits perfectly therein. Hollow cylinder 27 is further provided with an opening 29 serving to receive a thermocouple.

The thermocouple and the heating cartridge are connected to a temperature control device, not shown in the drawings.

In the embodiment shown, the heater 25 rests on a support 54 conveniently fixed to the metal chamber 24.

The entire assembly of heater 25 and chamber 24 is enclosed by a thermal insulation block 55.

The cylindrical shapes and interfitting positions as shown in FIGS. 3, 4, and 5 are merely given as examples and are in no way limiting the present invention. For instance, the cavities could also be of different cross sectional shapes, such as square, hexagonal, elliptical, and the like. It is merely required that the cavities be aligned as in the embodiment shown and permit the insertion of the parts providing for circulation of the various fluids and of the windows specified, apart from receiving the heating and measuring elements.

The apparatus described above can be used in detecting selectively chromatographic column effluents and also in detecting one or more classes of substances in a gaseous mixture. Classes of substances is designation for groups of compounds which belong to the same chemical function and so react with ozone on the same way, for instance, paraffinic, mono-olefinic, diolefinic and aromatic hydrocarbons.

Some examples will be described below for better explanation of the detecting possibilities offered by the detector and process according to the present invention. The examples given are merely illustrative and only serve as guidelines for better comprehension of the present invention, being in no way limitative.

When employing a chromatographic column, the components will be separated according to their affinity. However, because of the complexity of the mixture and the limited capacity of the chromatographic column, many hydrocarbons of various types cannot be distinguished. For instance a mono-olefin may be eluted with a paraffin, an aromatic with a diolefin and so on.

With the known hydrocarbon sensitive detectors there is no possibility of distinguishing between two hydrocarbons jointly eluted.

However, the detector and process according to the present invention permit such determination to be made.

(1) If the mixture consists of a paraffin and a mono-olefin and it is desired to determine the mono-olefin, it is sufficient to operate the reactor at a temperature which may be between 20° C. and 170° C., a range within which paraffins are not detected because under such conditions they are not able to react with ozone, whereas mono-olefins produce chemiluminescent radiation under these conditions.

(2) If it is desired to determine the diolefin in a mixture consisting of an aromatic and a diolefin, the temperature of the reaction chamber will be chosen between 20° C. and 100° C., a thermal range within which the aromatic will not be determined because aromatic compositions only emit luminosity in ozone reactions at temperatures above 100° C., while diolefin is easily detected under these conditions.

The spectrum obtained from the chemiluminescent reaction is characteristic of the substance producing it so that it can also be used as a means for the specific and selective determination of said substance. This is done by employing one or more optical filters or a monochromator for selecting the wavelength of the characteristic spectral bands of the desired substance which do not coincide with the bands produced by other substances which are likewise present.

If, as shown in the above example, a diolefin were eluted from the chromatographic column together with a mono-olefin, there would be no possibility of distinguishing them by means of varying the temperature of the reaction chamber since they both emit luminosity within the same temperature range. In this case the selectivity would be obtained by means of the optical system, by selecting the wavelength which is characteristic of the luminescence produced by a diolefin with ozone.

Thus only the diolefin would be detected because the mono-olefin does not emit luminescence in this band. On the other hand, if it is desired to determine the mono-olefin, the characteristic wavelength of the luminosity resulting from its reaction with ozone will be selected, and the diolefin will not interfere.

Figure 6:
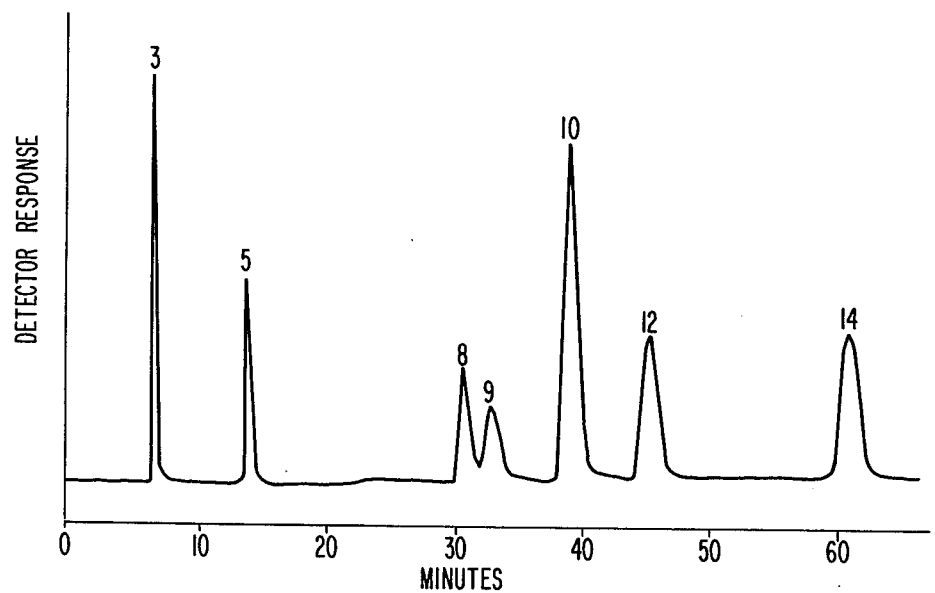
FIGS. 6 and 7 are representations of chromatograms obtained with the process according to the invention.
Figure 7:
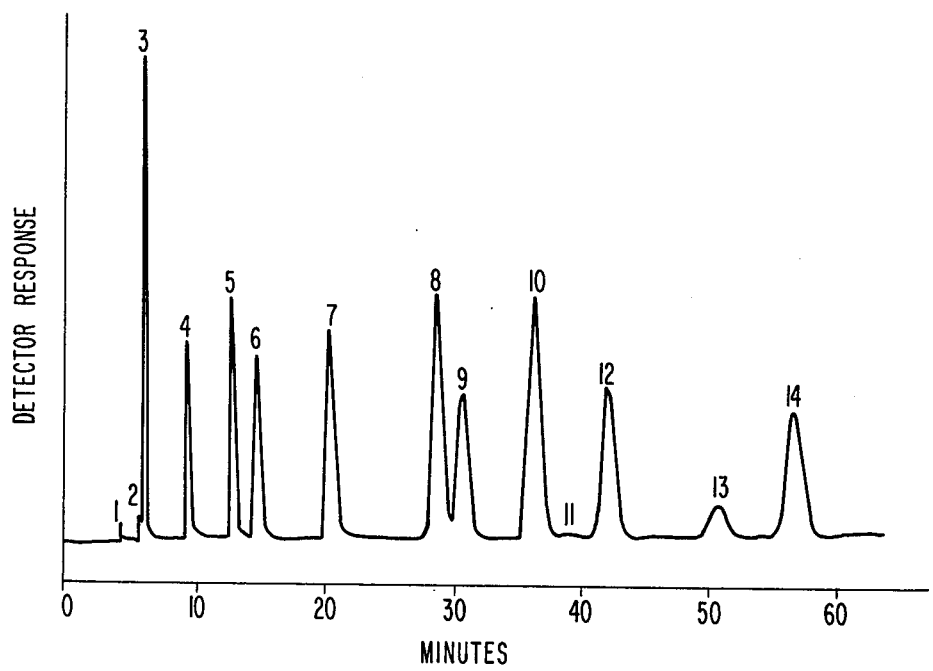

The application of the process and detector according to the invention is exemplified by FIGS. 6 & 7 which demonstrate that the detector of this invention is very flexible, selective and specific. By combining the selectivity of the reactivity of ozone with the various thermal emission characteristics of the reaction, the detector can be very specific for the chemical compound which it is desired to determine, provided that the chemical compound emits luminescence upon entering into contact with ozone.

FIGS. 6 and 7 show chromatograms obtained with the process according to the invention. A flow of hydrocarbons issuing from a chromatographic column was introduced into the reaction chamber together with ozone, such that the various components of the mixture reacted with the ozone to produce luminescence in the same sequence of separation in the chromatographic column.

In the example represented in FIG. 6 the reaction chamber of the detector according to the invention was kept at a temperature of 100° C., and determined the following components:
ethene—3
propene—5
1-butene—8
isobutene—9
2-trans butene—10
2-cis butene—12
1,3 butadiene—14

In the case of FIG. 7 the reaction chamber of the detector according to the invention was maintained at a temperature of 250° C. and determined the following components:
methane—1
ethane—2
ethene—3
propane—4
propene—5
isobutane—6
n-butane—7
butene—8
isobutene—9
2-trans butene—10
isopentane—11
2-cis butene—12
n-pentane—13
1,3 butadiene—14

It should be noted that the detector when operated at a temperature of 250° C. determines all the components of the mixture.

When the process and detector are not used for measuring the effluents from a chromatographic column, they can be employed as a specific means for determining organic compounds according to their chemical function, thus presenting a very useful method of carrying out a functional analysis of organic substances.

In this case the apparatus operates in two different ways:

(1) A temperature is chosen in such a way that only one class of substances contained in the gaseous mixture reacts with ozone. Thus, by varying the temperature, each class of substances can be detected successively. For instance, when the gaseous mixture contains saturated and unsaturated hydrocarbons and the reaction chamber is maintained at a temperature below 170° C., the detector will indicate the presence of the unsaturated hydrocarbons only. If the temperature is raised to above 170° C., the detector will indicate the presence of both saturated and unsaturated hydrocarbons, it thus being possible to determine the two classes of hydrocarbons separately without using filters or a monochromator.

(2) When the mixture has a high boiling point it is necessary to work at temperatures above 200° C. in order to vaporize it. In this temperature all classes of substances contained in the gaseous mixture react with ozone. Also in this case the detector works selectively determining qualitatively each class of substances in the gaseous mixture. This separation is best performed with the aid of a monochromator or filters.

As each class of substances emits chemiluminescence in a characteristic wavelength range, to detect each of these classes it is only necessary to determine the wavelength of greatest intensity that corresponds to each class. This determination is made by using a standard substance of each particular class.

If it is desired to detect one class of hydrocarbons, such as olefinic hydrocarbons, in the production line at a temperature in which all the other hydrocarbons contained in the mixture react with ozone, for instance temperatures above 200° C., the monochromator must be maintained in a wavelength range around 400 nm (4000 Å). Thus, only the olefinic hydrocarbons will be detected. Even if other hydrocarbons react with ozone, they will not interfere.

So, according to the present invention, when a gaseous mixture is used without any previous separation, it is possible to determine qualitatively and quantitatively the classes of substances which are present in the said gaseous mixture.

This possibility of applying the process according to the invention permits it to be utilized in the contamination control of industrial gas streams, at the same time offering the possibility of using the signal emitted for automatic control in a continuous process.

The detector according to the invention can be used in the determination of any organic or inorganic chemical substance capable of reacting with ozone in such a way as to produce luminescence which will be sensed by the detection system.

Detectable organic substances, among others, comprise:

(1) any kind of paraffinic, aromatic, cycloparaffinic, mono-olefinic, diolefinic, polyolefinic, acetylenic, polycyclic and the like hydrocarbons;

(2) any kind of oxygenated compound, such as alcohols, dihydric alcohols, polyhydric alcohols, aldehydes, ketones, acids, epoxides, acetals, ethers, esters, and the like;

(3) any kind of organic halogenated compound containing one or more chlorine, bromine, iodine or fluorine atoms and derived from any of the compositions cited under (1) or (2) above, (4) any kind of organic sulphurated compound, such as thiols, sulphides, disulphides, sulphonic acids, and the like;

(5) any kind of organic nitrogenated compound, such as nitriles, isocyanides, isocyanides, isocyanates, amines, amides, and the like;

Among the detectable inorganic substances, there are the following compounds: hydrogen, carbon monoxide, hydrogen sulphide gas, sulphur dioxide, carbon disulphide, carbonyl sulphide, nitric oxide, nitrous oxide and the like.

What is claimed is:

1. An apparatus for the qualitative and quantitative measurement of specific hydrocarbons contained in a mixture and capable of reacting with ozone to emit chemiluminescence, said apparatus comprising:

(a) a reaction chamber essentially comprising a cavity formed in an otherwise smooth phase of a metallic block, said cavity being closed by means of a quartz window fitted to said smooth phase to said metallic block, said block being formed with three orifices connecting the outside with the inside of the reaction chamber, one of said orifices being adapted for the admission to the inside of said chamber of the gaseous flow to be analyzed, another of said orifices being adapted to transmit the admission of ozone to the inside of said chamber and the third orifice being adapted for the discharge of the gases formed after the reaction with ozone;

(b) heating resistors inserted in said metallic block for maintaining said reaction chamber at a temperature selected between 20° and 250° C.;

(c) a gaseous mixture inlet tube fitted to said respective orifice in the metallic block, said tube being heated in a region before its point of fixture to the metallic block, said heating arrangement comprising a part of said tube being helically wound around an element heated by electrical resistors;

(d) a reaction gas outlet tube connected at one end to said reaction gas outlet orifice of the reaction chamber, and at the other end to means for treating said gases before discharge thereof in the atmosphere;

(e) a cooler comprising a metallic body provided throughout the extension of its central axis with an internal cavity, along which the light signal coming from the reaction chamber will pass, said cavity being closed at one of its ends by said quartz window of said reaction chamber and at its other end by a second quartz window, the walls of said metal body being provided with channels for the circulation of cooling liquid;

(f) means for detecting said chemiluminescence and providing a signal related to the intensity of said chemiluminescence, comprising an optical system adjacent said second quartz window, and a photomultiplier adjacent said optical system, the internal cavity of said cooler, said quartz window in said reaction chamber, said optical system and said photomultiplier being optically aligned with each other; and (g) electronic amplifier, converter and recorder means for said signal connected to said photomultiplier.

2. Apparatus according to claim 1, in which the optical system comprises a light radiation selector filter.

3. Apparatus according to claim 1, in which the optical system comprises an optical mask provided with a variable slit.

4. Apparatus according to claim 1, including external means for controlling the heating of said metallic block, which forms the reaction chamber, and the cylindrical heating element for heating said gaseous mixture inlet tube.

* * * * *